United States Patent
Schropp, Jr. et al.

(10) Patent No.: US 8,117,897 B2
(45) Date of Patent: Feb. 21, 2012

(54) ELLIPTICAL PHOTO-ACOUSTIC SENSOR

(75) Inventors: Donald R. Schropp, Jr., Austin, TX (US); Igor Pavlovsky, Cedar Park, TX (US); Richard Lee Fink, Austin, TX (US)

(73) Assignee: Applied Nanotech Holdings, Inc., Austin, TX (US)

(*) Notice: Subject to any disclaimer, the term of this patent is extended or adjusted under 35 U.S.C. 154(b) by 757 days.

(21) Appl. No.: 11/944,892

(22) Filed: Nov. 26, 2007

(65) Prior Publication Data
US 2008/0121018 A1    May 29, 2008

Related U.S. Application Data

(60) Provisional application No. 60/867,361, filed on Nov. 27, 2006.

(51) Int. Cl.
*G01P 9/02*    (2006.01)
*G01N 21/00*    (2006.01)

(52) U.S. Cl. .................. 73/24.01; 73/24.02; 250/343

(58) Field of Classification Search ............. 73/24.01, 73/23.22, 23.35, 23.36, 23.37, 23.4, 23.41, 73/23.42, 24.02, 24.03, 24.04, 24.05, 24.06; 250/343, 344, 345

See application file for complete search history.

(56) References Cited

U.S. PATENT DOCUMENTS

| | | | | |
|---|---|---|---|---|
| 3,179,898 A * | 4/1965 | Meltzer | ............ | 372/72 |
| 3,266,313 A * | 8/1966 | Litterst | ............ | 374/130 |
| 3,588,739 A * | 6/1971 | Yoshikawa et al. | ............ | 372/72 |
| 3,745,325 A * | 7/1973 | Harvey | ............ | 362/6 |
| 3,946,239 A * | 3/1976 | Salzman et al. | ............ | 250/461.2 |
| 4,188,543 A * | 2/1980 | Brunsting et al. | ............ | 250/458.1 |
| 4,457,162 A * | 7/1984 | Rush et al. | ............ | 73/24.01 |
| 4,557,603 A * | 12/1985 | Oehler et al. | ............ | 356/418 |
| 4,657,397 A * | 4/1987 | Oehler et al. | ............ | 356/414 |
| 4,740,086 A * | 4/1988 | Oehler et al. | ............ | 356/432 |
| 4,771,629 A * | 9/1988 | Carlson et al. | ............ | 73/23.35 |
| 4,818,882 A * | 4/1989 | Nexo et al. | ............ | 250/343 |
| 5,170,064 A * | 12/1992 | Howe | ............ | 250/573 |
| 5,753,797 A * | 5/1998 | Forster et al. | ............ | 73/24.01 |
| 5,973,326 A * | 10/1999 | Parry et al. | ............ | 250/343 |
| 6,006,585 A * | 12/1999 | Forster | ............ | 73/24.01 |
| 6,694,799 B2 * | 2/2004 | Small | ............ | 73/24.02 |
| 6,843,102 B1 * | 1/2005 | Shulga et al. | ............ | 73/25.01 |
| 6,897,960 B2 * | 5/2005 | DiMeo et al. | ............ | 356/437 |
| 7,069,769 B2 * | 7/2006 | Kung | ............ | 73/24.02 |
| 7,213,444 B2 * | 5/2007 | Baraket et al. | ............ | 73/24.01 |
| 7,263,871 B2 * | 9/2007 | Selker et al. | ............ | 73/24.02 |
| 7,488,942 B2 * | 2/2009 | Hopkins et al. | ............ | 250/343 |

* cited by examiner

*Primary Examiner* — Helen C. Kwok
(74) *Attorney, Agent, or Firm* — Kelly Kordzik; Matheson Keys Garsson & Kordzik PLLC

(57) ABSTRACT

An elliptical photo-acoustic spectrometer chamber design will result in a larger intensity signal at the pick-up microphone and allow high frequency light modulation. This makes the spectrometer have a lower limit of detection threshold, and will increase the signal to noise ratio in general for the instrument, resulting in a more sensitive instrument allowing more precise measurements.

18 Claims, 6 Drawing Sheets

ELLIPTICAL PHOTO-ACOUSTIC SENSOR

CROSS-REFERENCE TO RELATED APPLICATIONS

This application claims priority to U.S. Application Ser. No. 60/867,361, filed on Nov. 27, 2006.

BACKGROUND

A photo-acoustic spectrometer (PAS) is an instrument to measure trace gases, which operates by illuminating the gas with modulated light resonant with the species of interest in a small chamber. The light energy is absorbed, usually exciting molecular vibrational modes. Via collisional exchange, the vibrational energy is transferred to increased molecular kinetic energy, equivalent to a local rise in macroscopic temperature. The local temperature increase induces a pressure wave, which propagates throughout the small chamber and is measured by a microphone.

In a non-resonant chamber the acoustic pressure is $P=K(C_p/C_v-1)I/f$; where $K$ is a constant depending on the cell geometry and gas; $C_p$ and $C_v$ are the gas specific heats at constant pressure and volume, respectively; $I$ is the light intensity; and $f$ is the light modulation frequency. That the acoustic pressure depends on the period of the light modulation implies there is no well definable acoustic wave front, but rather the entire volume of gas is being heated over a time $T/2$ where $T$ is $f^{-1}$. Typically $f \sim 25$ Hz. Physically, the pressure inside the chamber is increasing and decreasing at that frequency. At atmospheric pressure and typical chamber length scales of 1 cm the corresponding acoustic frequency would be 33 kHz.

In a resonant photo-acoustic spectrometer, the light is modulated at a frequency equal to a natural resonant frequency of the chamber. For a cube chamber geometry this would be a standing wave mode, with the lowest frequency mode having a wavelength twice the cube's linear dimension. Typical modulation frequencies for resonant chambers are in the kilohertz range. Resonant chambers pump up the standing wave in a coherent fashion, resulting in higher pressure levels and larger microphone signals. Resonant chamber spectrometers can have signal-to-noise ratios orders of magnitude higher than their non-resonant counterparts.

A problem is that for a non-resonant case the modulation frequencies must be low to provide a chamber pressure level detectable by the microphone. At low frequencies, external vibrational noise amplitudes are higher. Secondly, the wave nature of pressure propagation is not capitalized on. For a traveling sine wave, instantaneous nodes of zero pressure amplitude must be balanced by antinodes with a much higher pressure amplitude to maintain average energy density. The resulting larger amplitude provides a larger microphone signal, which is absent in the non-resonant case.

DESCRIPTION OF DRAWINGS

The details of one or more embodiments of the invention are set forth in the accompanying drawings and the description below. Other features, objects, and advantages of the invention will be apparent from the description and drawings, and from the claims.

Like reference symbols in the various drawings indicate like elements.

DETAILED DESCRIPTION

Figure 1:
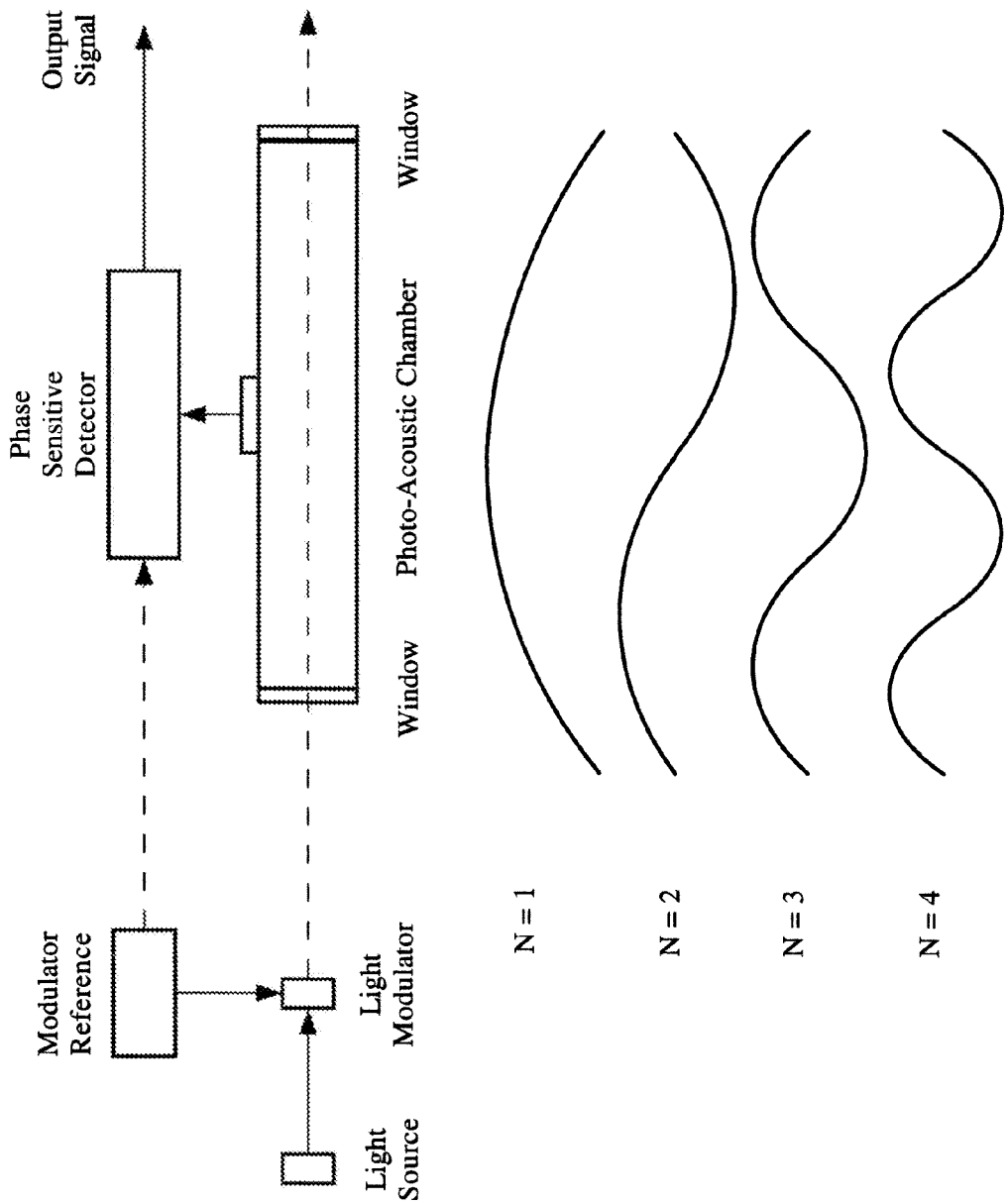
FIG. 1 illustrates a photo-acoustic sensor.

With respect to the resonant case, resonant chamber geometries have been simple in design; cylindrical is a common choice. That makes exciting a single mode optimized for detector placement difficult if not impossible. Current designs typically place the pick-up microphone at the halfway point along the cylinder z-axis and are sensitive to whatever amount of amplitude is present in the fundamental longitudinal mode and possibly its odd harmonics. FIG. 1 illustrates a resonant PAS design, and its first four longitudinal resonant modes. Energy is also distributed among the unshown transverse modes.

The Photo-Acoustic chamber is a gas volume enclosed by a high rigidity material to have minimal deformation by surface pressure. This results in maximal reflection of an acoustic pressure wave from each surface, giving the chamber a high Q factor. Any cell geometry will have an infinite series of resonant modes and a corresponding resonant frequency. Optimal cell design insures that the resonant mode of intended operation will be well separated in frequency from any neighboring modes to avoid energy loss to modes with frequencies outside the phase detection bandwidth. The chamber windows may have 100% transmission at the excitation light wavelength to prevent absorptive heating and subsequent acoustic excitation at the chamber resonant frequency. Acoustic excitation from absorptive window loss would mimic a desired gas detection signal and reduce the real signal-to-noise ratio.

The Light Source provides excitation light at a resonant optical absorption frequency of the trace gas species of interest. It is narrow band to minimize excitation of interfering gas species with overlapping absorption spectral lines. Multifrequency light may be provided by using broadband light sources and appropriate filters or narrow band tunable light sources. The excitation light is modulated by the Light Modulator, typically in an on-off fashion using a chopper wheel or an electro-optic modulator deriving its signal from the Modulator Reference. The frequency of the on-off light modulation is chosen to match the acoustic resonance mode that the Photo-Acoustic Chamber is designed for. When the light modulation frequency is matched with the chamber acoustic resonant frequency, the acoustic resonant mode is pumped up in amplitude until the input absorptive light energy equals the dissipative energy losses of the Photo-Acoustic Chamber. A high Q (low energy loss per acoustic cycle) chamber is thus desired to maximize the pressure amplitude of the acoustic resonant mode. The pressure amplitude of the acoustic resonant mode is then sensed by the Microphone coupled to the acoustic chamber. The Microphone signal and the Modulator Reference signal are processed together using a Phase Sensitive Detector to extract the acoustic resonant amplitude resulting from the optical absorption resonance of the trace gas species of interest. The Phase Sensitive Detector Output Signal is then proportional to the trace gas species concentration.

Part of a solution is to excite a single resonant mode with a correspondingly optimized detector placement. The result of doing that, in conjunction with a small chamber, will impose a second part of the solution: higher frequency operation. These goals may be accomplished via the following embodiments.

Elliptical Chamber Design

Figure 2:
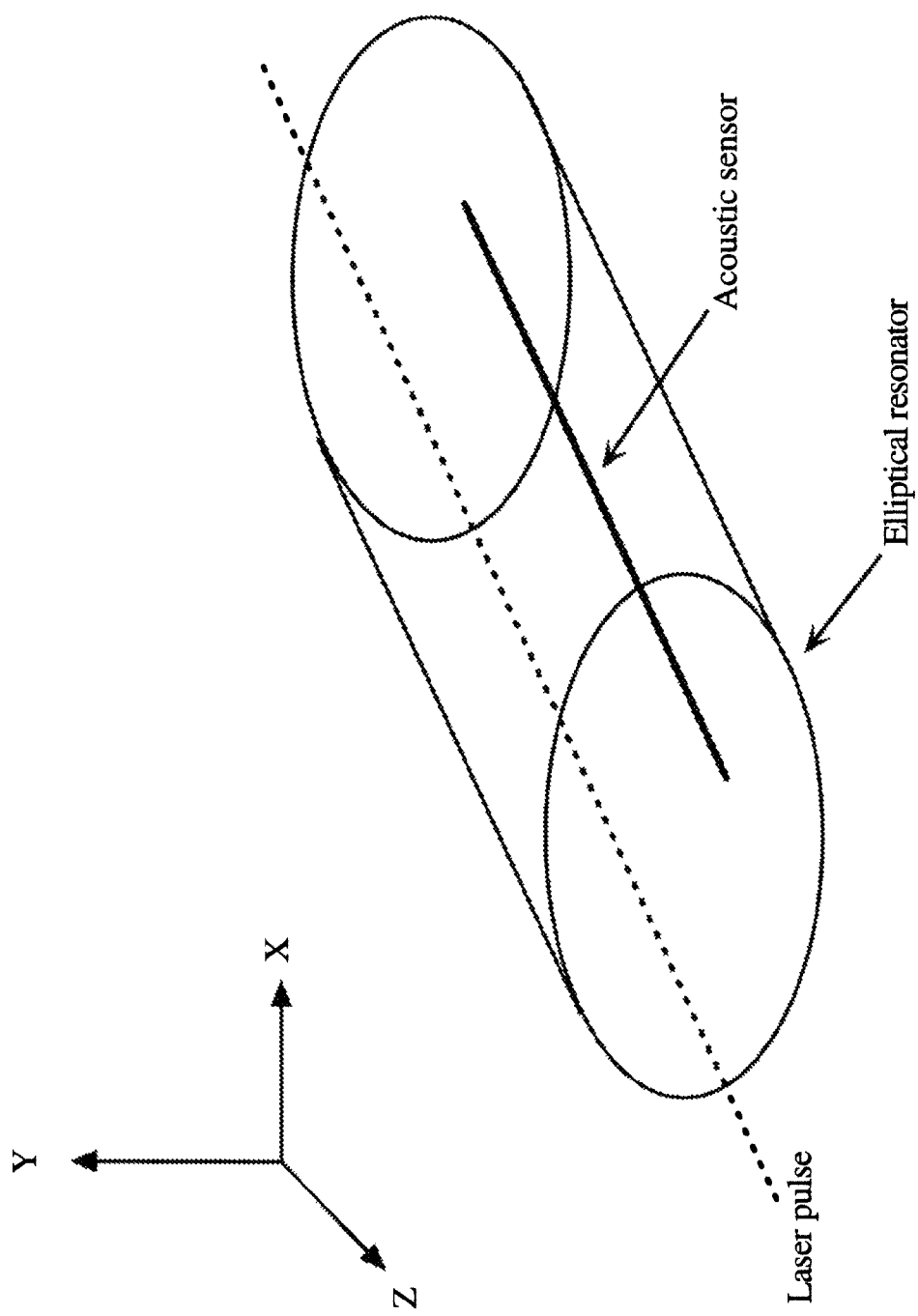
FIG. 2 illustrates a schematic of an elliptical chamber for a photo-acoustic sensor.
Figure 3:
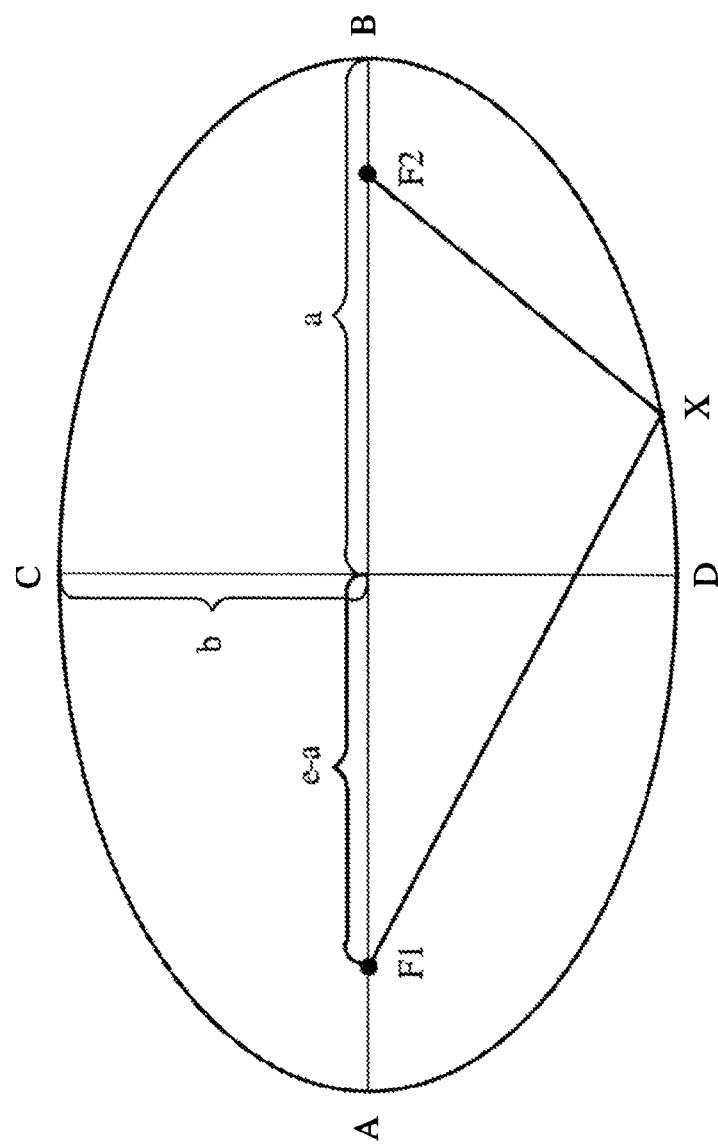
FIG. 3 illustrates a geometry of a cross-section of the elliptical chamber of FIG. 2.

In one embodiment, the path lengths are arranged from the excitation region to the pick-up microphone to be the same. This is accomplished by using an elliptical chamber with the light excitation path oriented along one focus and the pick-up microphone oriented along the other focus. Such an elliptical chamber will replace the cylindrical one in FIG. 1. FIG. 2 shows a geometry of an axially extended elliptical chamber. The excitation light is pulsed along one focus, and an extended acoustic sensor (e.g., microphone) is placed along the second focus. By definition and construction, the path length from focus F1 to the ellipse wall to focus F2 is constant. FIG. 3 shows the geometry of an ellipse, where the distance F1-X-F2 is a constant. Also, when a traveling wave is reflected from a more dense medium at an interface, here the cavity wall, the impinging wave undergoes a 180° reflection. But all the wave paths induce one reflection so the same phase shift occurs for all wavelets and coherence is maintained.

A single constant, the eccentricity e, defines the shape of the ellipse and is the ratio of the semi-major axis a to the ellipse-center-to-focus length. The path length F1-ellipse-F2 is 2a, so if the speed of sound in the chamber gas is c, after a time 2a/c a delta function excitation at F1 will converge at F2, and after 4a/c will reconverge on F1 again. The delta function excitation and reconvergence of the line pressure pulse is actually a superposition of all transverse modes for the elliptical cavity. For a small resonator chamber with semi-major axis a=1 cm, and atmospheric sound velocity of 330 m/s, the round trip time for a signal generated at F1 to reconverge on F1 is 60.6 μs, or a rate of 16.5 kHz. That leads to the following embodiment.

Fast Resonant Light Pulsing

If a short light pulse is repeated at the above resonant rate along focus F1, the approximately delta function pulse will gain in amplitude until the cavity energy loss per cycle equals the light energy absorbed by the gas. That is the rise time to reach maximal amplitude of the 16.5 kHz traveling wave pulse, and will produce maximal pressure levels alternately at foci F1 and F2. Now the pressure level at F2 needs to be sensed, which may be performed in accordance with any of the following embodiments.

Figure 4:
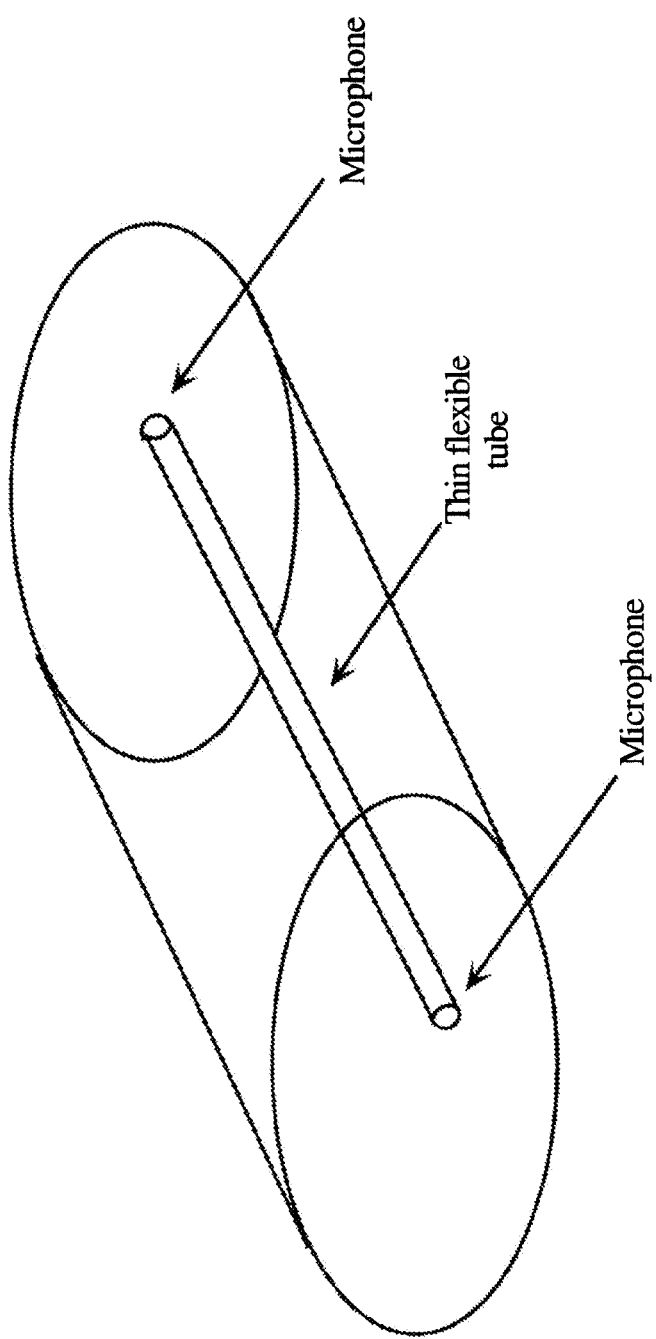
FIGS. 4-6 illustrate various embodiments of the present invention.
Figure 5:
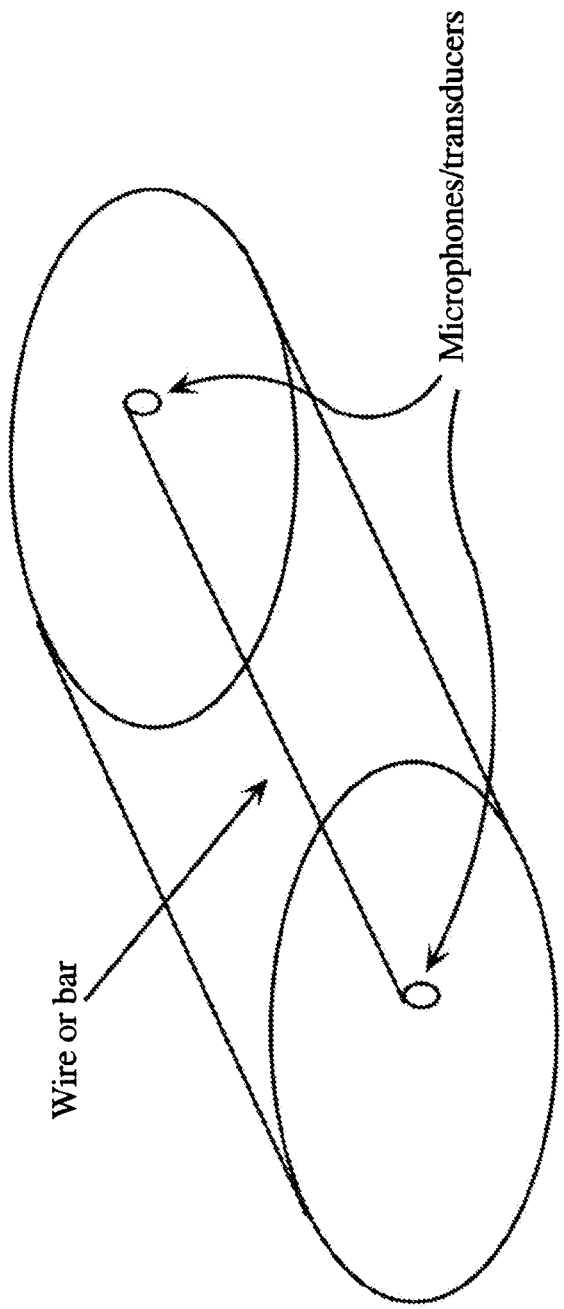

Sensing a Line-Like Pressure a) Coupling the pressure increase to two microphones: This embodiment uses a thin, flexible tube oriented along the acoustic sensor line (F2) in FIG. 2, with its ends attached to two microphones. See FIG. 4. The pressure increase converging on F2 increases the pressure in the tube, which may itself be slightly overpressured to maintain mechanical rigidity, to maximally transmit the acoustic energy to the microphones.

b) Use of a rigid mechanical pick-up: Instead of redirecting the pressure wave as above, a rigid mechanical bar (similar to a thin pencil lead) may be aligned along the acoustic sensor line (F2) as in FIG. 2 and coupled (e.g., glued) to two microphones. See FIG. 5. The bar/rod may be aligned slightly off but parallel to the F2 focus. The impinging acoustic wave will strike one side sooner than the other resulting in a large jolt, which will be picked up by the microphones.

c) Use of a second wavelength probing laser: A second laser having a frequency non-resonant with the gas species of interest but resonant with the background gas may be aimed along the acoustic sensing path at F2, with a sensing photodiode placed at the opposite end of the chamber in an absorption spectroscopy configuration.

Figure 6:
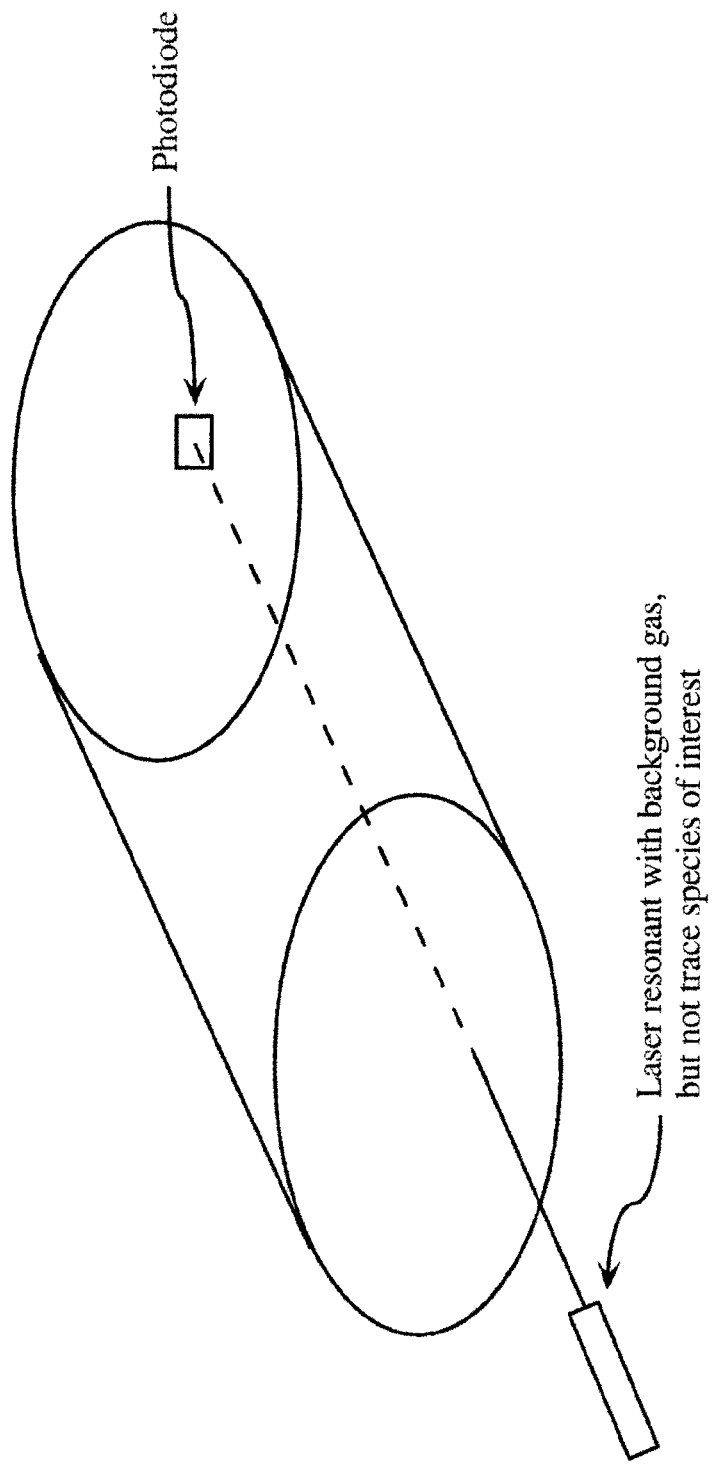

See FIG. 6. The probe light absorption will depend on the density (via the pressure) of the background gas, so the photodiode signal will decrease with increasing pressure along the light probe path.

A number of embodiments of the invention have been described. Nevertheless, it will be understood that various modifications may be made without departing from the spirit and scope of the invention. Accordingly, other embodiments are within the scope of the following claims.

What is claimed is:

1. A photo-acoustic sensor comprising:
an elliptically shaped chamber having its two foci positioned along its longitudinal axis;
a light excitation path oriented along a first focus of the chamber; and
an acoustic sensor oriented along a second focus of the chamber.

2. The sensor as recited in claim 1, further comprising a trace gas inside of the chamber to be sensed.

3. The sensor as recited in claim 2, further comprising a laser for transmitting a laser pulse along the light excitation path.

4. The sensor as recited in claim 3, wherein a frequency of the laser pulse is modulated to resonate with the gas.

5. The sensor as recited in claim 1, wherein the acoustic sensor comprises a flexible tube oriented along the second focus with its ends connected to microphones.

6. The sensor as recited in claim 1, wherein the acoustic sensor comprises a rigid mechanical pick-up substantially oriented along the second focus and coupled to microphones.

7. The sensor as recited in claim 1, wherein the acoustic sensor comprises a probing laser signal aimed along the second focus, wherein a frequency of the probing laser signal is resonant with a background gas containing a trace gas to be sensed, the probing laser signal aimed to strike a photodiode positioned on an end wall of the chamber.

8. The sensor as recited in claim 1, wherein the elliptically shaped chamber comprises a cylinder having a cross-section that is in a shape of an ellipse, wherein the two foci are positioned along the longitudinal axis of the cylinder.

9. The sensor as recited in claim 1, wherein the elliptically shaped chamber comprises an elliptical cylinder.

10. The sensor as recited in claim 2, wherein the trace gas is present along the first focus of the chamber.

11. The sensor as recited in claim 1, wherein for a cross-section of the chamber perpendicular to the longitudinal axis of the chamber, a path length measured from the first focus to any position along a wall of the chamber to the second focus is constant.

12. A photo-acoustic sensor comprising:
an axially extended elliptical chamber having first and second axially extended foci;
a light excitation path oriented along a length of the first axially extended focus of the chamber; and
an extended acoustic sensor positioned along a length of the second axially extended focus of the chamber.

13. The sensor as recited in claim 12, further comprising a trace gas present along the first axially extended focus of the chamber.

14. The sensor as recited in claim 13, further comprising a laser for transmitting a laser pulse along the light excitation path.

15. The sensor as recited in claim 12, wherein the acoustic sensor comprises a flexible tube oriented along the second axially extended focus with its ends connected to microphones.

16. The sensor as recited in claim 12, wherein the acoustic sensor comprises a rigid mechanical pick-up substantially oriented along the second axially extended focus and coupled to microphones.

17. The sensor as recited in claim 12, wherein the acoustic sensor comprises a probing laser signal aimed along the second axially extended focus, wherein a frequency of the probing laser signal is resonant with a background gas containing a trace gas to be sensed, the probing laser signal aimed to strike a photodiode positioned on an end wall of the chamber.

18. The sensor as recited in claim 12, wherein for a cross-section of the chamber perpendicular to the longitudinal axis of the chamber, a path length measured from the first focus to any position along a wall of the chamber to the second focus is constant.

* * * * *